(12) United States Patent
Song et al.

(10) Patent No.: US 12,186,138 B2
(45) Date of Patent: Jan. 7, 2025

(54) AUGMENTED REALITY HEADSET FOR A SURGICAL ROBOT

(71) Applicant: Verb Surgical Inc., Santa Clara, CA (US)

(72) Inventors: Tianyu Song, Mountain View, CA (US); Blade Olson, Pasadena, CA (US); Bernhard A. Fuerst, Sunnyvale, CA (US); Danyal Fer, Oakland, CA (US)

(73) Assignee: Verb Surgical Inc., Santa Clara, CA (US)

( * ) Notice: Subject to any disclaimer, the term of this patent is extended or adjusted under 35 U.S.C. 154(b) by 979 days.

(21) Appl. No.: 17/039,949

(22) Filed: Sep. 30, 2020

(65) Prior Publication Data

US 2022/0096197 A1  Mar. 31, 2022

(51) Int. Cl.
*A61B 90/00* (2016.01)
*A61B 34/37* (2016.01)
(Continued)

(52) U.S. Cl.
CPC ............. *A61B 90/36* (2016.02); *A61B 34/37* (2016.02); *G06T 7/70* (2017.01); *G06T 17/20* (2013.01);
(Continued)

(58) Field of Classification Search
CPC ........ A61B 90/36; A61B 34/37; A61B 90/37; A61B 2034/102; A61B 2034/2065;
(Continued)

(56) References Cited

U.S. PATENT DOCUMENTS

| 11,723,739 B2 | 8/2023 | Asadian et al. |
| 2020/0054412 A1 | 2/2020 | Fuerst et al. |

(Continued)

FOREIGN PATENT DOCUMENTS

| EP | 3533409 | 9/2019 |
| WO | 2018148845 | 8/2018 |
| WO | 2020072302 | 4/2020 |

OTHER PUBLICATIONS

International Search Report and Written Opinion for International Application No. PCT/IB2021/058785 mailed Dec. 24, 2021, 9 pages.
(Continued)

*Primary Examiner* — Ryan R Yang
(74) *Attorney, Agent, or Firm* — Aikin & Gallant, LLP

(57) ABSTRACT

Disclosed is an augmented reality (AR) headset that provides a wearer with spatial, system, and temporal contextual information of a surgical robotic system to guide the wearer in configuring, operating, or troubleshooting the surgical robotic system prior to, during, or after surgery. The spatial context information may be rendered to display spatially-fixed 3D-generated virtual models of the robotic arms, instruments, bed, and other components of the surgical robotic system that match the actual position or orientation of the surgical robotic system in the AR headset's coordinate frame. The AR headset may communicate with the surgical robotic system to receive real-time state information of the components of the surgical robotic system. The AR headset may use the real-time state information to display context-sensitive user interface information such as tips, suggestions, visual or audio cues on maneuvering the robotic arms and table to their target positions and orientations or for troubleshooting purpose.

20 Claims, 9 Drawing Sheets

(51) Int. Cl.
*G06T 7/70* (2017.01)
*G06T 17/20* (2006.01)
*G06T 19/00* (2011.01)
*A61B 34/10* (2016.01)
*A61B 34/20* (2016.01)
*A61B 34/30* (2016.01)
*A61B 90/50* (2016.01)

(52) U.S. Cl.
CPC ...... *G06T 19/006* (2013.01); *A61B 2034/102* (2016.02); *A61B 2034/2065* (2016.02); *A61B 2034/301* (2016.02); *A61B 2090/365* (2016.02); *A61B 90/37* (2016.02); *A61B 2090/502* (2016.02); *G06T 2207/30204* (2013.01)

(58) Field of Classification Search
CPC ........ A61B 2034/301; A61B 2090/365; A61B 2090/502; A61B 90/361; A61B 34/20; A61B 34/30; A61B 90/96; A61B 2090/372; G06T 7/70; G06T 17/20; G06T 19/006; G06T 2207/30204; G06T 2210/41
See application file for complete search history.

(56) References Cited

U.S. PATENT DOCUMENTS

| | | |
|---|---|---|
| 2020/0126661 A1 | 4/2020 | Flexman et al. |
| 2021/0192759 A1* | 6/2021 | Lang ..................... A61B 34/20 |
| 2021/0241517 A1* | 8/2021 | Segal ..................... G06T 7/70 |

OTHER PUBLICATIONS

Qian, L., et al., "ARssist: augmented reality on a head-mounted display for the first assistant in robotic surgery," Healthcare Technology Letters, Aug. 20, 2018, vol. 5, No. 5, pp. 194-200.

Cao, A., et al., "Image-based marker tracking and registration for intraoperative 3D image-guided interventions using augmented reality," 2019, pp. 1-5.

* cited by examiner

AUGMENTED REALITY HEADSET FOR A SURGICAL ROBOT

TECHNICAL FIELD

The subject technology generally relates to robotics and surgical systems, and more specifically to an augmented reality headset to guide a user of a robotically-assisted surgical system to setup surgical robotic arms or other components of the robotically-assisted surgical system when preparing or performing minimally invasive surgeries.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. In robotic MIS systems, it may be desirable to establish and maintain high positional accuracy for surgical instruments supported by the robotic arms.

Medical staff and personnel typically setup the robotic arms prior to the start of surgery. Importantly, the robotic arms must be in the correct pose relative to a patient; otherwise, complications can come about during surgery. Setup of the robotic arms and more generally the robotic system is a complicated and tedious task, often requiring an expansive professional education team to train new operating room staff on how to properly configure the pose of the robotic arms for surgery. The medical staff may also need to troubleshoot setup of the robotic arms or the attached surgical tools when issues arise. Prior training on how to troubleshoot may be easily forgotten, especially when the scenarios are rare.

During surgery, control of the robotic arms may require control inputs from a user (e.g., surgeon or other operator) via one or more user interface devices that translate manipulations or commands from the user into control of the robotic arms. For example, in response to user commands, a tool driver having one or more motors may actuate one or more degrees of freedom of a surgical tool when the surgical tool is positioned at the surgical site in the patient. Sometimes during surgery, it becomes necessary for the medical staff to quickly move the robotic arms away from the patient such as when the patient's vitals drop dramatically. Complications may arise when prior training on how to manipulate the robotic arms in emergency situations may be easily forgotten. Moving the wrong robotic arm may cause severe harm to the patient, other equipment, or bedside personnel.

As such, it is desirable to have a tool that eases the complexity of training for new users, reduces the cost of hiring and training a dedicated education team, prevents delay in robotic system setup, and eliminates catastrophes that may result from user confusion during troubleshooting or emergency scenarios. The tool may be used by medical staff to minimize mistakes when preparing and performing robotically-assisted surgeries.

SUMMARY

Disclosed herein is an augmented reality headset that may be donned to provide real-time spatial and contextual information to guide medical staff when setting up and operating a robotically-assisted surgical system, also referred to as a surgical robotic system, which is a software-controlled, electro-mechanical system designed for surgeons to perform minimally-invasive surgeries. The augmented reality headset may overlay spatially-fixed, 3D-generated models and contextually relevant user-interface information of the surgical robotic system onto a visor. A wearer of the augmented reality headset may receive intuitive guidance on the tasks needed to prepare components of the surgical robotic system, such as the robotic arms, for surgery. For example, a wearer may receive spatial information such as the location and orientation of the robotic arms, system state information such as the arm modes, tool types, tool grasp status, and other real-time information of the robotic arms, and temporal contextual information for effecting movement of the robotic arms.

The augmented reality headset may include a sensor, a processor, and a display. The sensor may capture image data of a component such as a robotic arm or an operating table of the surgical robotic system. The processor may establish a common coordinate frame between the augmented reality device and the surgical robotic system based on the image data. The augmented reality headset may communicate with the surgical robotic system to receive spatial information and real-time system state information of the surgical robotic system. The processor may create a 3D virtual model of another component of the surgical robotic system, which may be the same or a different component as the component whose image data was taken. The 3D virtual model is created in a coordinate frame of the augmented reality headset based on the spatial information and the real-time system state information of the surgical robotic system, and based on the common coordinate frame between the augmented reality device and the surgical robotic system. The display may present the 3D virtual model of the component to a wearer of the augmented reality headset.

A method for an augmented reality headset to interact with the surgical robotic system is disclosed. The method includes the augmented reality headset capturing image data of a component such as an arm or an operating table of the surgical robotic system. The method also includes establishing by the augmented reality headset, based on the image data, 3D position and orientation of the surgical robotic system in the coordinate frame of the augmented reality headset. The method further includes receiving by the augmented reality headset spatial information and real-time system state information of the surgical robotic system. The method further includes creating by the augmented reality headset the 3D virtual model of another component of the surgical robotic system in a coordinate frame of the augmented reality headset based on the spatial information and the real-time system state information of the surgical robotic system, and based on the 3D position and orientation of the surgical robotic system in the coordinate frame of the augmented reality headset. The method further includes the augmented reality headset maintaining the 3D virtual model of the component as the coordinate frame of the AR device changes relative to a coordinate frame of the surgical robotic system.

BRIEF DESCRIPTION OF THE DRAWINGS

The accompanying drawings are provided together with the following description of various aspects and embodiments of the subject technology for a better comprehension of the invention. The drawings and the embodiments are illustrative of the invention, and are not intended to limit the scope of the invention. It is understood that a person of ordinary skill in the art may modify the drawings to generate drawings of other embodiments that would still fall within the scope of the invention.

DETAILED DESCRIPTION

Examples of various aspects and variations of the subject technology are described herein and illustrated in the accompanying drawings. The following description is not intended to limit the invention to these embodiments, but rather to enable a person skilled in the art to make and use this invention.

Disclosed is an augmented reality (AR) headset that provides a wearer with spatial, system, and temporal contextual information of components of a surgical robotic system to guide the wearer in configuring and troubleshooting the surgical robotic system prior to, during, or after surgery. The spatial context information may be rendered to display spatially-fixed 3D-generated virtual models of the robotic arms, instruments, bed, and other components of the surgical robotic system that match the real-time actual position or orientation of the surgical robotic system in the AR headset's coordinate frame. A simultaneous localization and mapping (SLAM) algorithm may run on the AR headset to localize the position and orientation of the AR headset so the virtual models of the surgical robotic system are rendered to maintain the actual position and orientation of the surgical robotic system as the wearer moves about in the operating room. In one embodiment, virtual models representing the desired or target position and orientation of the robotic arm may be rendered to overlay the actual position and orientation of the robotic arm. The virtual models may be used to guide the wearer of the AR headset to move the robotic arm from the current to the target position and orientation.

The AR headset may also communicate with the surgical robotic system to receive real-time state information of the components of the surgical robotic system. The AR headset may use the state information to display context-sensitive user interface information to guide the wearer in configuring, operating, or troubleshooting the surgical robotic system. In one embodiment, the state information of the surgical robotic system may include a robotic arm's joint angles, tool type, tool grasp status, active tool energy, arm mode, troubleshooting codes, etc. In one embodiment, the state information may include position, orientation, angle, operating mode, etc., of the bed. The AR headset may display tips, suggestions, visual or audio cues, etc., on how to manually move, or execute an automated sequence to robotically guide, a robotic arm into a target position without hitting obstacles, patient, bed, or other robotic arms.

Figure 1:
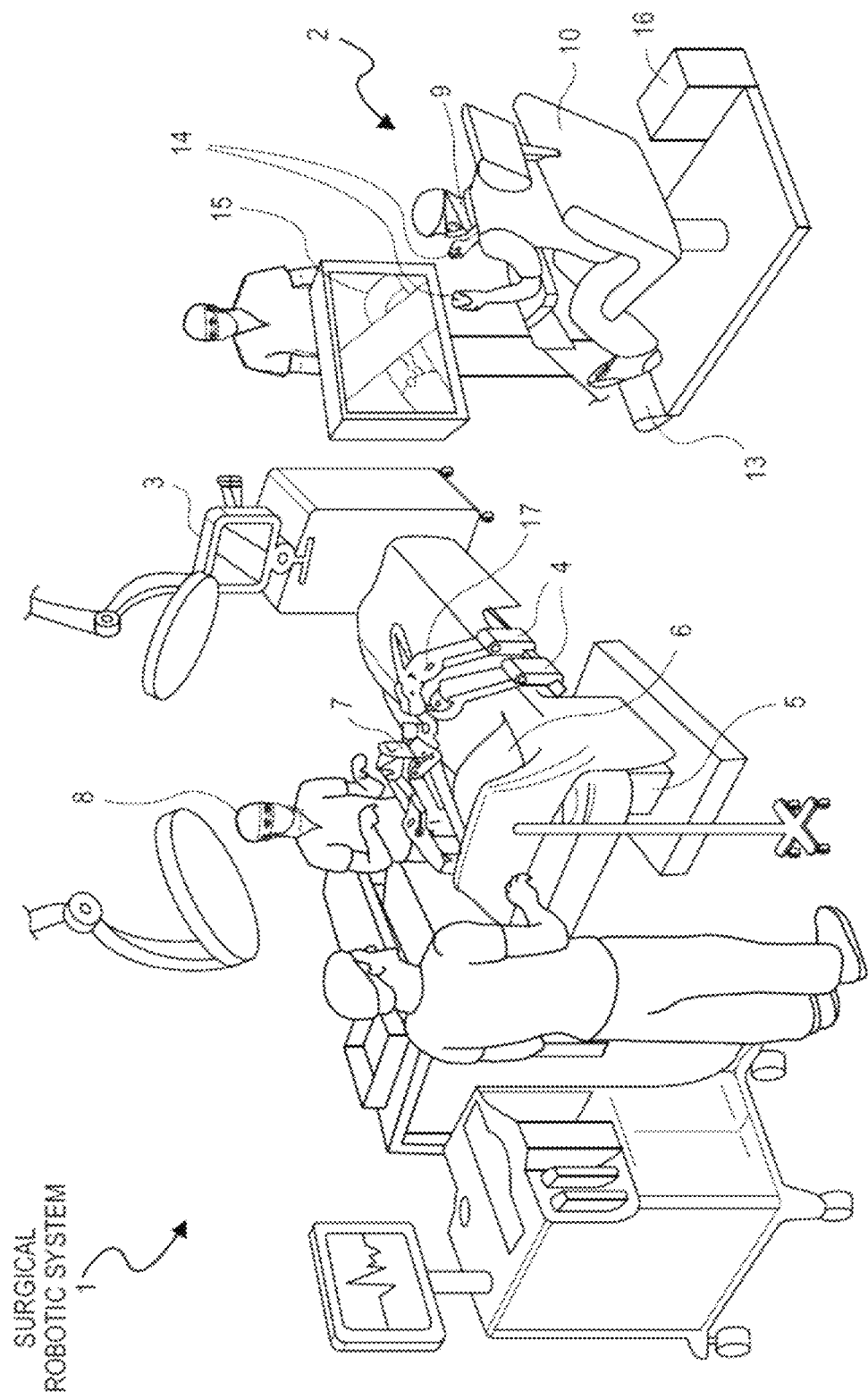
FIG. 1 is a pictorial view of an example surgical robotic system 1 in an operating arena, in accordance with aspects of the subject technology.

FIG. 1 is a pictorial view of an example surgical robotic system 1 in an operating arena, in accordance with aspects of the subject technology. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or another person, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4).

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. For example, the remote operator 9 at the user console 2 or the bedside operator 8 may use the handheld UIDs 14 to move the arm 4 from the stowed configuration to a preparation position above the patient 6 during the pre-operative setup. Alternatively, a surgeon or bedside personnel with a direct view of the table 5 may wear the AR headset disclosed herein to receive guidance on moving the arm 4. For example, the AR headset may render a virtual image of the actual stowed configuration of the arm 4, a virtual image of the desired preparation position, and a series of waypoints to guide the surgeon or bedside personnel on how to move the arm 4 from the current stowed configuration to the preparation position.

Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table 5, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2. During the surgery or the post-operative procedures, bedside personnel may wear the AR headset disclosed herein to receive guidance in performing manual or automated repositioning of the arms 4.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table 5 to the right side of the patient, and a left arm 4 that is at the left side of the patient. An actuator 17 may include one or more motors that are controlled so that they drive the rotation of a joint of the arm 4 to, for example, change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that are transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Prior to initiating surgery with the surgical robotic system 1, the surgical team can perform the preoperative setup. During the preoperative setup, the main components of the surgical robotic system (table 5 and robotic arms 4, control tower 3, and user console 2) are positioned in the operating room, connected, and powered on. The table 5 and robotic arms 4 may be in a fully-stowed configuration with the arms 4 under the table 5 for storage and/or transportation purposes. The surgical team can extend the arms from their stowed position for sterile draping. After draping, the arms 4 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 4 over the patient and attach each arm to its corresponding sleeve. In one embodiment, guidance for maneuvering the arms 4 to safely attach to the corresponding sleeves or tools may be provided by AR headsets worn by members of the surgical team. The AR headsets may render virtual images of the target positions and orientations of the arms 4 and a series of waypoints for maneuvering the arms 4 from their current positions and orientations to the target position and orientations. The surgical robotic system 1 has the capability to uniquely identify each tool (endoscope and surgical instruments) as soon as it is attached and display the tool type and arm location on the open or immersive display 15 at the user console 2 and the touchscreen display on the control tower 3. The corresponding tool functions are enabled and can be activated using the master UIDs 14 and foot pedals 13. The patient-side assistant can attach and detach the tools, as required, throughout the procedure. The surgeon seated at the user console 2 can begin to perform surgery using the tools controlled by two master UIDs 14 and foot pedals 13. The system translates the surgeon's hand, wrist, and finger movements through the master UIDs 14 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 14 for instrument alignment and continue instrument control and motion. The foot pedals 13 may be used to activate various system modes, such as endoscope control and various instrument functions including monopolar and bipolar cautery, without involving surgeon's hands removed from the master UIDs 116.

The table 5 can be repositioned intraoperatively. For safety reason, all tool tips should be in view and under active control by the surgeon at the user console 2. Instruments that are not under active surgeon control must be removed, and the table feet must be locked. During table motion, the integrated robotic arms 4 may passively follow the table movements. Audio and visual cues can be used to guide the surgery team during table motion. Audio cues may include tones and voice prompts. Visual messaging on the displays at the user console 2 and control tower 3 can inform the surgical team of the table motion status.

Figure 2:
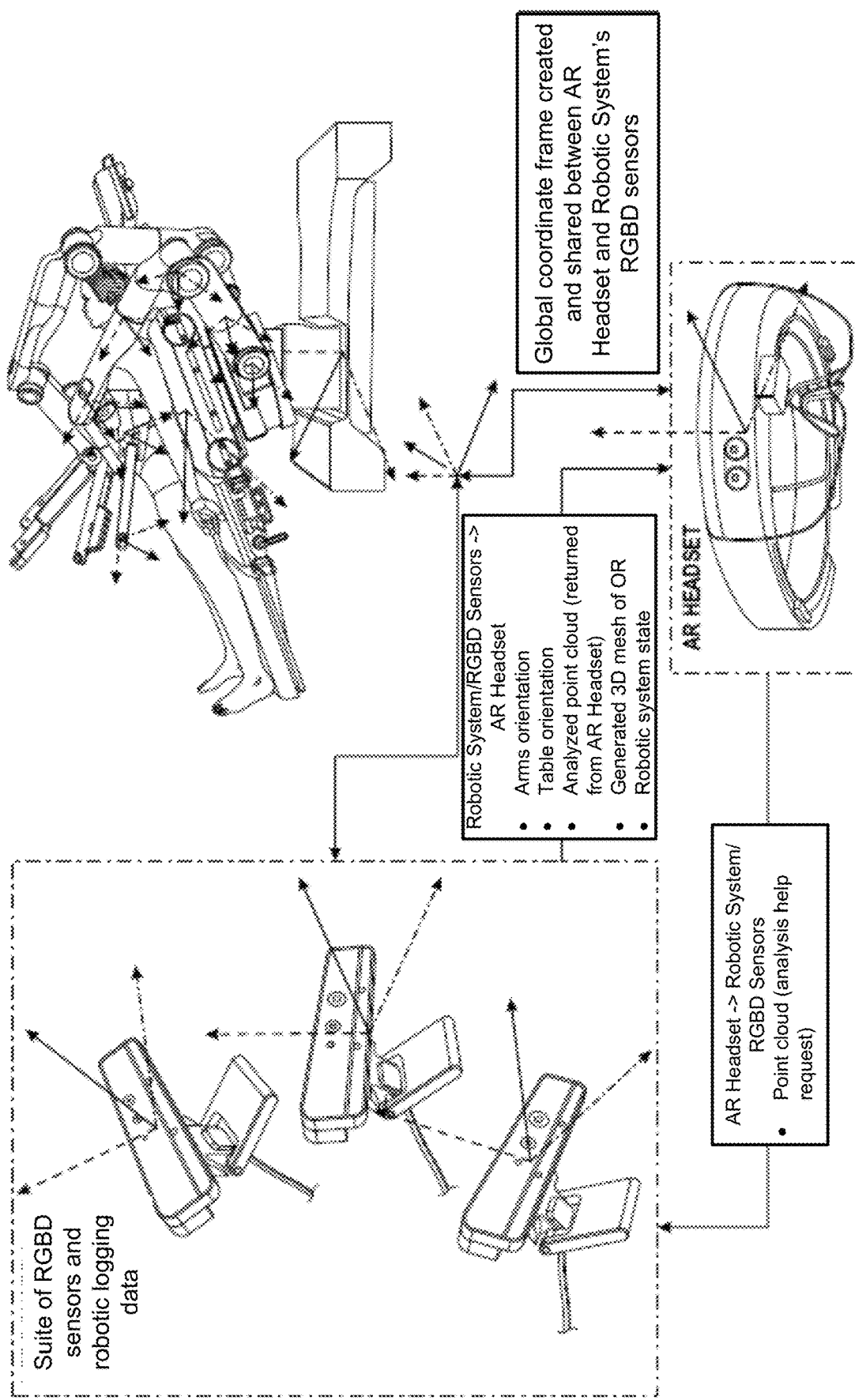
FIG. 2 shows the information exchange between an augmented reality headset and a surgical robotic system for the augmented reality headset to display spatial, system, and temporal information of the components of the surgical robotic system based on establishing a common coordinate frame between the augmented reality headset and the surgical robotic system using image sensors, in accordance with aspects of the subject technology.

FIG. 2 shows the information exchange between an augmented reality headset and a surgical robotic system for the AR headset to display spatial, system, and temporal information of the components of the surgical robotic system based on establishing a common or global coordinate frame between the AR headset and the surgical robotic system using image sensors, in accordance with aspects of the subject technology. The AR headset may have one or more cameras that capture color and depth information of real scene objects. For example, the AR headset may have RGB and depth (RGBD) sensors to capture color images and depth-image information of the arms 4 and table 5 of the surgical robotic system 1 from the perspective of the wearer of the AR headset. The RGBD image captured by the AR headset is thus an image of the real-scene arms 4 and table 5 based on the coordinate frame of the AR headset. In one embodiment, the AR headset may run an object recognition algorithm to recognize the arms 4 and table 5. The surgical robotic system 1 may have a suite of RGBD sensors installed at various locations to capture color images and depth information of the configuration of the arms 4 and table 5. The RGBD images captured by the surgical robotic system 1 are thus the images of the arms 4 and the 5 based on the coordinate frame of the surgical robotic system 1. For the AR headset to render virtual recreation of the arms 4 and table 5 that matches the real-time real-scene positions and orientations of the arms 4 and table 5, or to render virtual images of the arms 4 and table 5 that may be fused with the real-time real-scene positions and orientations of the arms 4 and table 5, a common coordinate frame may be established between the AR headset and the surgical robotic system 1. In one embodiment, the surgical robotic system 1 may have other types of sensors such as infrared sensors to capture images and other information of the arms 4 and table 5 of the surgical robotic system 1 or the patient.

The AR headset may transmit the RGBD image, also referred as the point cloud, to the surgical robotic system 1, such as the control tower 3, to request assistance in analyzing the point cloud. The surgical robotic system 1 may process the analyzed point cloud from the AR headset, the RGBD images captured by the surgical robotic system 1, and real-time data stream that describes the position and orientation information of the arms 4 and table 5 to recognize and virtually establish the 3D positions and orientations of the arms 4 and table 5 in the AR headset's coordinate frame. Thus, surgical robotic system 1 may establish a common or global coordinate frame between the AR headset and the surgical robotic system 1. Based on the common coordinate frame, the surgical robotic system 1 may transmit information to the AR headset for the AR headset to create 3D virtual models of the arms 4 and table 5 that match their actual positions and orientations, or to create 3D virtual models of the arms 4 and table 5 that may be fused with their real-time real-scene positions and orientations. The surgical robotic system 1 may transmit the global coordinate frame to the AR headset.

Information that the surgical robotic system 1 transmits to the AR headset may include real-time information of the positions and orientations of the arms 4 and the table 5, analyzed results of the point cloud received from the AR headset, 3D mesh model of components of the surgical robotic system 1 or the operating room, real-time system state information of the surgical robotic system 1, etc. In one embodiment, the real-time system state information may include joint angles and degrees of rotations of the arms 4, types of tools attached to the arms 4, tool grasp status, active tool energy, arm mode (e.g., stowed configuration, preparation pose, clutch mode, teleoperation control, etc.), troubleshooting error codes, etc. Using the information received from the surgical robotic system 1, the AR headset may render virtual images of the arms 4, table 5, or other components of the surgical robotic system 1 or of the operating room to be fused with real-scene objects captured by the RGBD sensors in the AR headset's coordinate frame.

A simultaneous localization and mapping (SLAM) algorithm may run on the AR headset to localize the position and orientation of the AR headset so the virtual images of the components of the surgical robotic system 1 are spatially-fixed to maintain their virtual positions and orientations as the wearer moves about in the operating room. For example, virtual recreation of the arms 4 and table 5 may match the real-time real-scene positions and orientations of the arms 4 and table 5 as the coordinate frame of the AR headset changes relative to the coordinate frame of the surgical robotic system 1. In addition to rendering the real-time spatial information of the surgical robotic system 1, using the state information received from the surgical robotic system 1, the AR headset may render real-time system information of the surgical robotic system 1 that the RGBD sensors and computer vision algorithm cannot detect. The spatial, system, and temporal context-sensitive information of the surgical robotic system 1 provided by the AR headset may be used to guide the wearer in configuring, operating, or troubleshooting the surgical robotic system 1 prior to, during, or after surgery.

Figure 3:
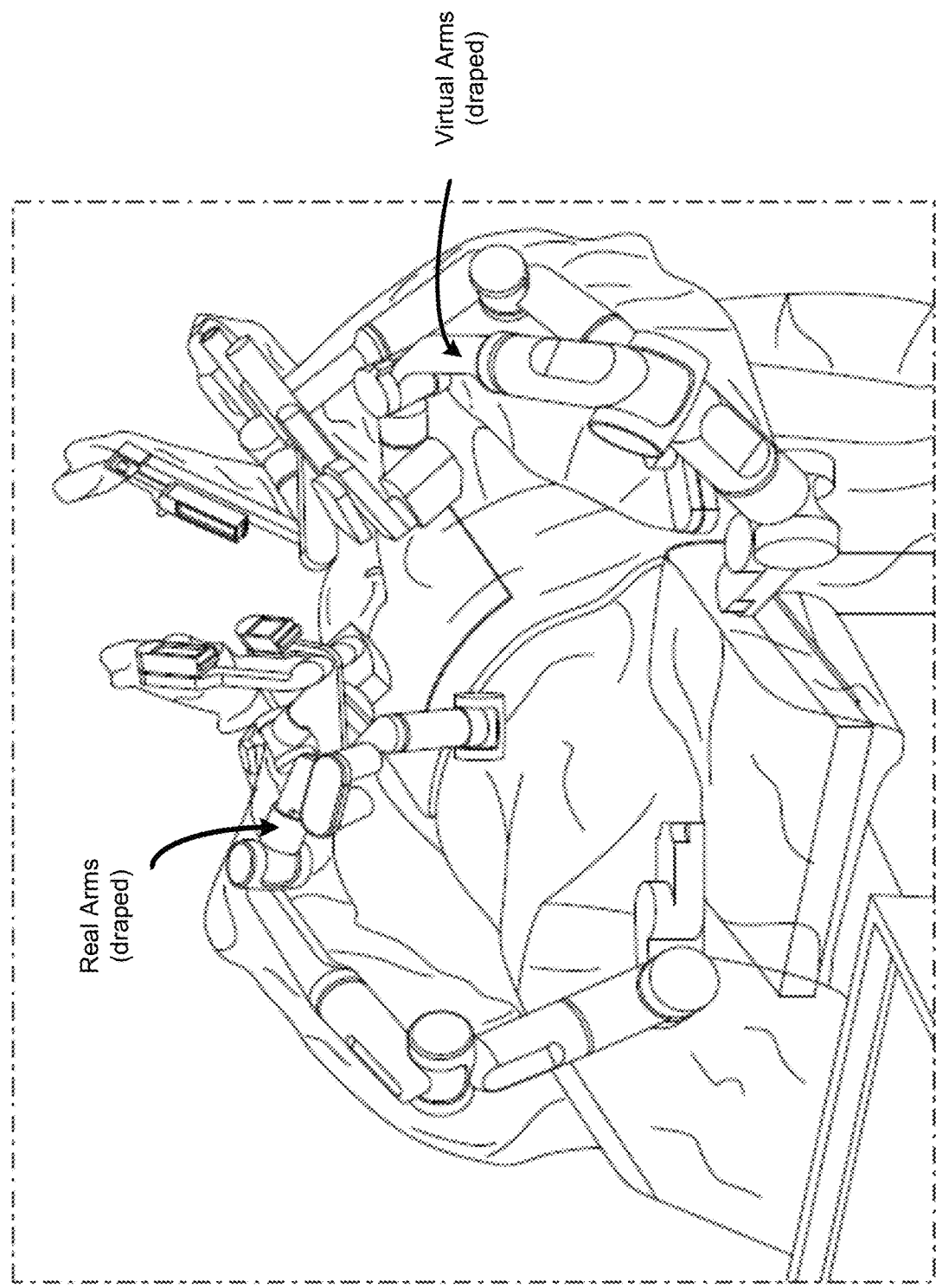
FIG. 3 shows a hologram rendered by the augmented reality headset showing the actual and the target pose of a robotic arm to guide medical staff in moving the robotic arm to the target pose, in accordance with aspects of the subject technology.

FIG. 3 shows a hologram rendered by the augmented reality headset showing the actual and the target pose of a robotic arm to guide medical staff in moving the robotic arm to the target pose, in accordance with aspects of the subject technology. The robotic arm may be extended in a draped pose for sterile draping. The AR headset may recreate a virtual image of the arm (labeled real arm) to match its real-time position and orientation in the draped pose. In one embodiment, the AR headset may project the real-scene arm captured by the RGBD sensor. It is desired to move the arm to its preparation pose above the patient during pre-operative setup, such as in a maneuver to dock the arm to a trocar.

The AR headset may receive information from the surgical robotic system on the target position and orientation of the arm in the preparation pose for the AR headset to render a virtual image of the arm in the preparation pose (labeled virtual arm). The image of the real arm and the image of the virtual arm may maintain their relative pose as the coordinate frame of the AR headset changes due to the wearer's movement. In one embodiment, if the arm is to be moved robotically from its current draped pose to the preparation pose, the AR headset may receive information from the surgical robotic system on a trajectory generated by a robotic control algorithm for moving the arm. The AR headset may generate a series of virtual images of the arm as it is guided by the robotic control algorithm along the trajectory from the draped pose to the preparation pose. The bedside personnel wearing the AR headset may confirm that the arm may move along the trajectory unimpeded by potential obstacles before commanding the surgical robotic system to execute the robotic control algorithm to move the arm.

In one embodiment, if the arm is to be moved manually to the preparation pose, the AR headset may receive information from the surgical robotic system on a recommended trajectory for moving the arm to avoid hitting other obstacles, the patient, bedside personnel, table, other arms, etc. The AR headset may generate a series of waypoints to guide the bedside personnel on how to move the arm. The waypoints may be rendered as a series of virtual images of the arm as when moving the arm robotically. The bedside personal may maneuver the arm to align with the virtual images of the arm along the recommended trajectory and finally into the target pose.

Figure 4:
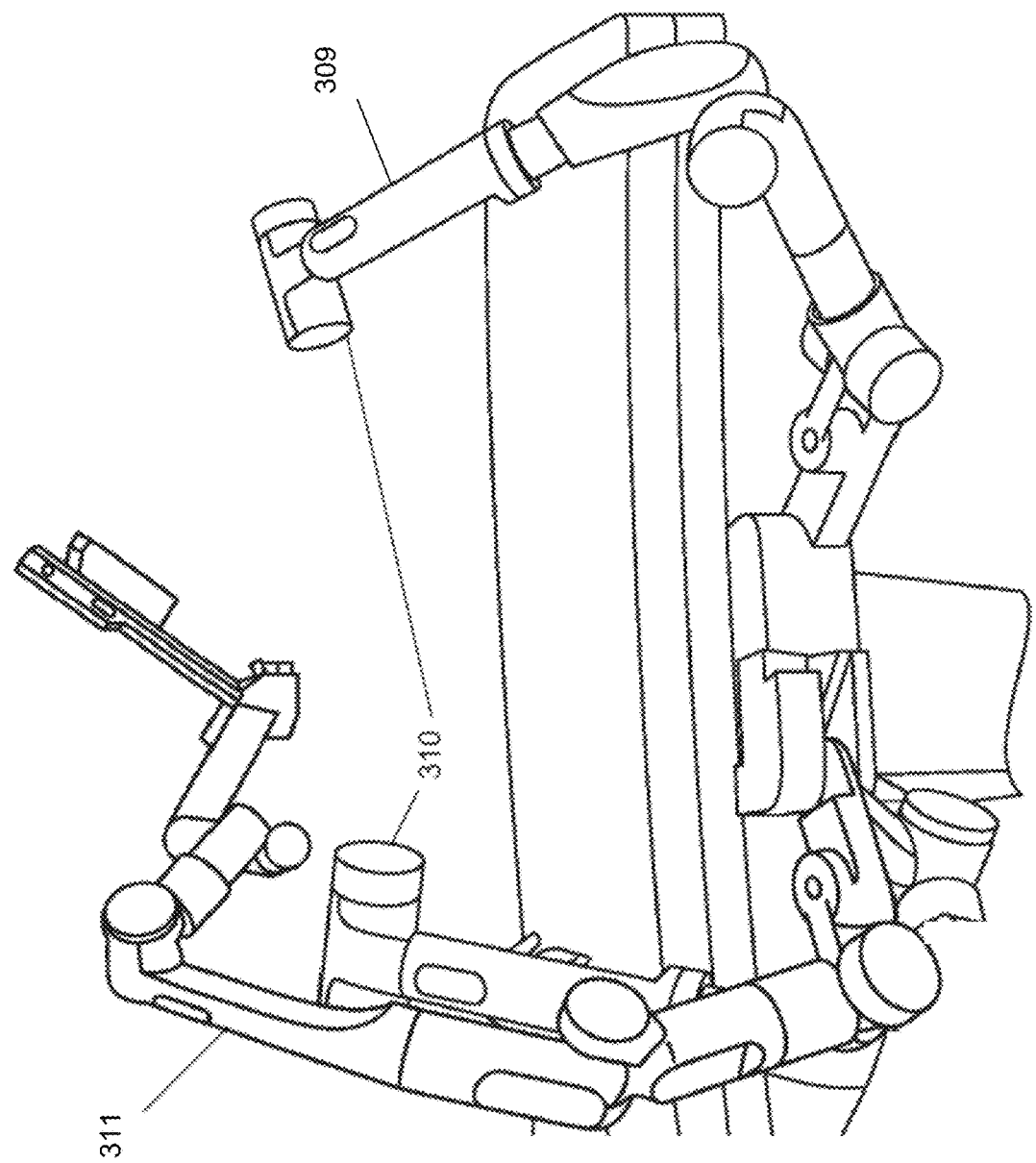
FIG. 4 shows the actual pose and the target pose of a robotic arm that may be used to generate waypoints as rendered on the augmented reality headset to guide medical staff in moving the robotic arm from the actual pose to the target pose, in accordance with aspects of the subject technology.

FIG. 4 shows the actual pose and the target pose of a robotic arm that may be used to generate waypoints as rendered on the augmented reality headset to guide medical staff in moving the robotic arm from the actual pose to the target pose, in accordance with aspects of the subject technology. The arm in its current pose 309 may be rendered as a virtual image or projected as a real-scene object captured by the RGBD sensor. The arm is also rendered as a virtual arm 311 in its target pose. The arm is to be moved along a trajectory 310 to the target pose of the virtual arm 311. The AR headset may render the virtual arm 311 at the same anchor/mount point as the arm in its current pose 309, thus giving the real and virtual robotic arms a common anchored reference point. In one embodiment, the AR headset may render the trajectory 310 as a series of waypoints or a series of virtual images of the arm. The bedside personnel wearing the AR headset may maneuver the arm from the current pose 309 along the waypoints or to align with the virtual images of the trajectory 310 until the arm finally aligns with the virtual arm 311 in its target pose. When the arm is at or within a tolerance of the target pose, the AR headset may respond with an indication to the user such as by highlighting the arm. The AR headset may also render visual cues or generate audio cues to help the user to maneuver the arm along the trajectory 310.

In one embodiment, the AR headset may provide context-sensitive information to guide a user to move an arm out of the way of other arms. For example, prior to the surgery or during surgery, when the surgeon is only using three arms for the surgery, the AR headset may highlight a "free arm movement" button on a 4th arm for bedside personnel to disengage the arm from its preparation or pre-docking pose and to safely move the arm away from the three other arms and the bed 5.

In one embodiment, the AR headset may provide information on whether surgical tools have been correctly connected to the arms 4 and other context-sensitive troubleshooting information. For example, the AR headset may receive system state information from the surgical robotic system 1 on the type of tools attached to the arms 4 and the identification of the arms 4 with the tools attached. When a tool has been properly attached to an arm, the AR headset may highlight the arm or the tool in blue to visually indicate to the user that the tool is operational. When an arm or the tool attached to the arm is not highlighted blue or is highlighted in red, the user is warned to troubleshoot the incorrectly attached tool. In one embodiment, the AR headset may display troubleshooting codes or generate audio guidance to assist the user in diagnosing the problem.

In one embodiment, the AR headset may provide guidance to bedside personnel on how to handle emergency situations. For example, if the patient's vitals have dropped dramatically and the robotic arms 4 have to be moved away from the patient quickly to allow intervention measures, the AR headset may provide critical guidance to bedside personnel. The AR headset may receive instructions from the surgical robotic system 1 on the sequence of operations to release the tools, disengage the arms 4 from the docked positions, and maneuver the arms 4 away from the patient. The AR headset may guide the bedside personnel through the sequence of operations using context-sensitive real-time information such as highlighting buttons on the arms 4, displaying text, or providing other types of visual or audio instructions on how to quickly move the arms 4 without causing harm to the patient, other equipment, or bedside personnel. Thus, the AR headset may provide guidance on emergency procedures that may have been forgotten by the bedside personnel, eliminating catastrophes that could result from user confusion or mistakes in emergency situations.

In one embodiment, the AR headset may show the impact of the current pose such as providing information on the workspace of the arms 4 or the tools attached to the arm 4. The AR headset may receive from the surgical robotic system 1 information on the maximum and minimum reach of the arms 4 or the tools as the arms 4 or the tools are currently positioned and oriented. The AR headset may render an image of the workspace volume to help the bedside personnel to position the arm 4 or the tool with greater precision. In one embodiment, the AR headset may receive a 3D scan of the patient from the surgical robotic system 1. The AR headset may render an image of a trocar based on the 3D scan to guide the bedside personnel to position the arm to dock with the trocar.

Figure 5:
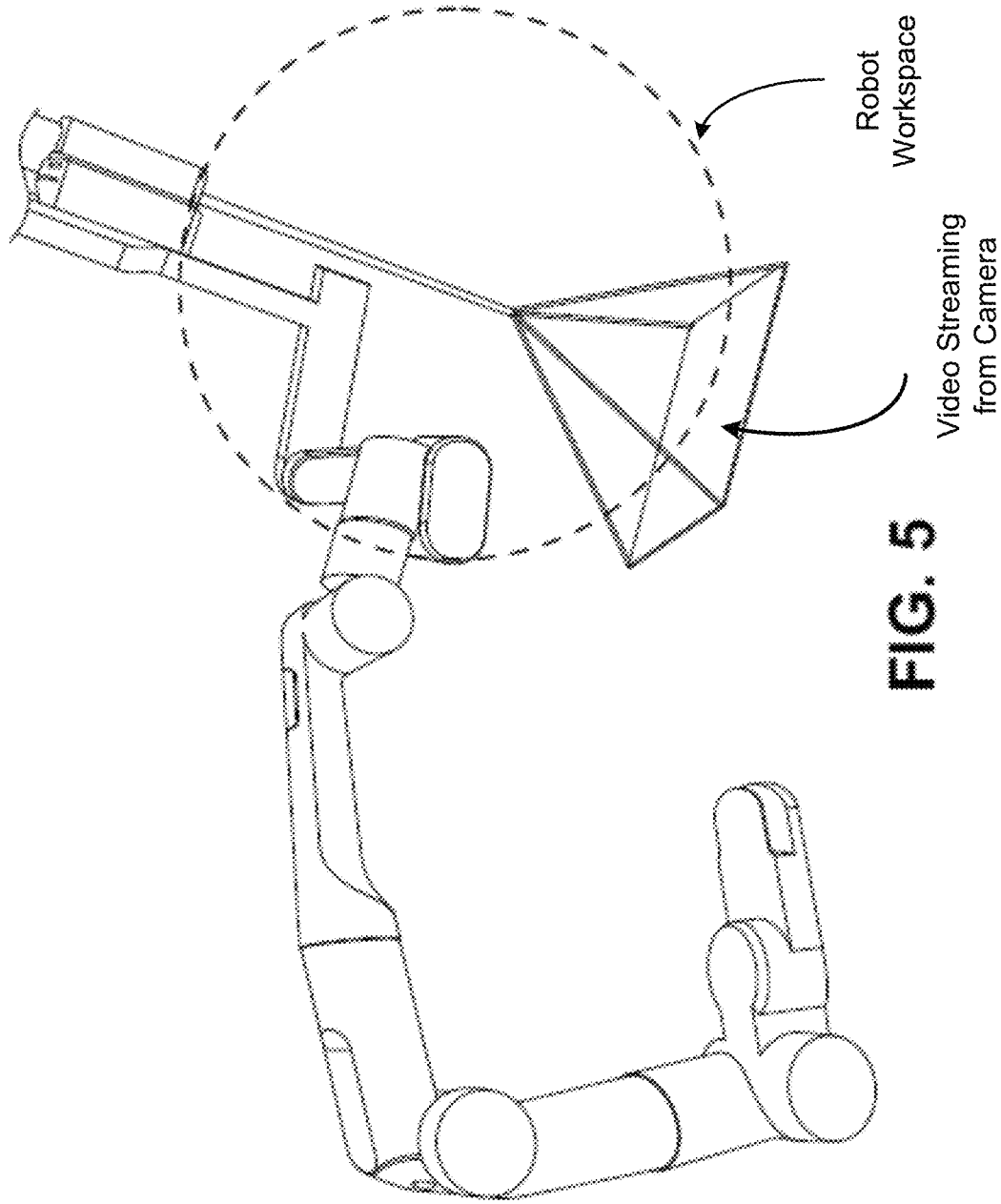
FIG. 5 shows a hologram rendered by the augmented reality headset highlighting a workspace of a robotic arm and the attached endoscope to help medical staff to position the robotic arm, in accordance with aspects of the subject technology.

FIG. 5 shows a hologram rendered by the AR headset highlighting a workspace of a robotic arm and the attached endoscope to help medical staff to position the robotic arm, in accordance with aspects of the subject technology. The hologram may guide a user in positioning the arm and the endoscope to provide camera visualization when setting up the starting positon for the surgery. The hologram may display the viewing angle and the video stream from the camera relative to the endoscope's position and orientation.

Figure 6:
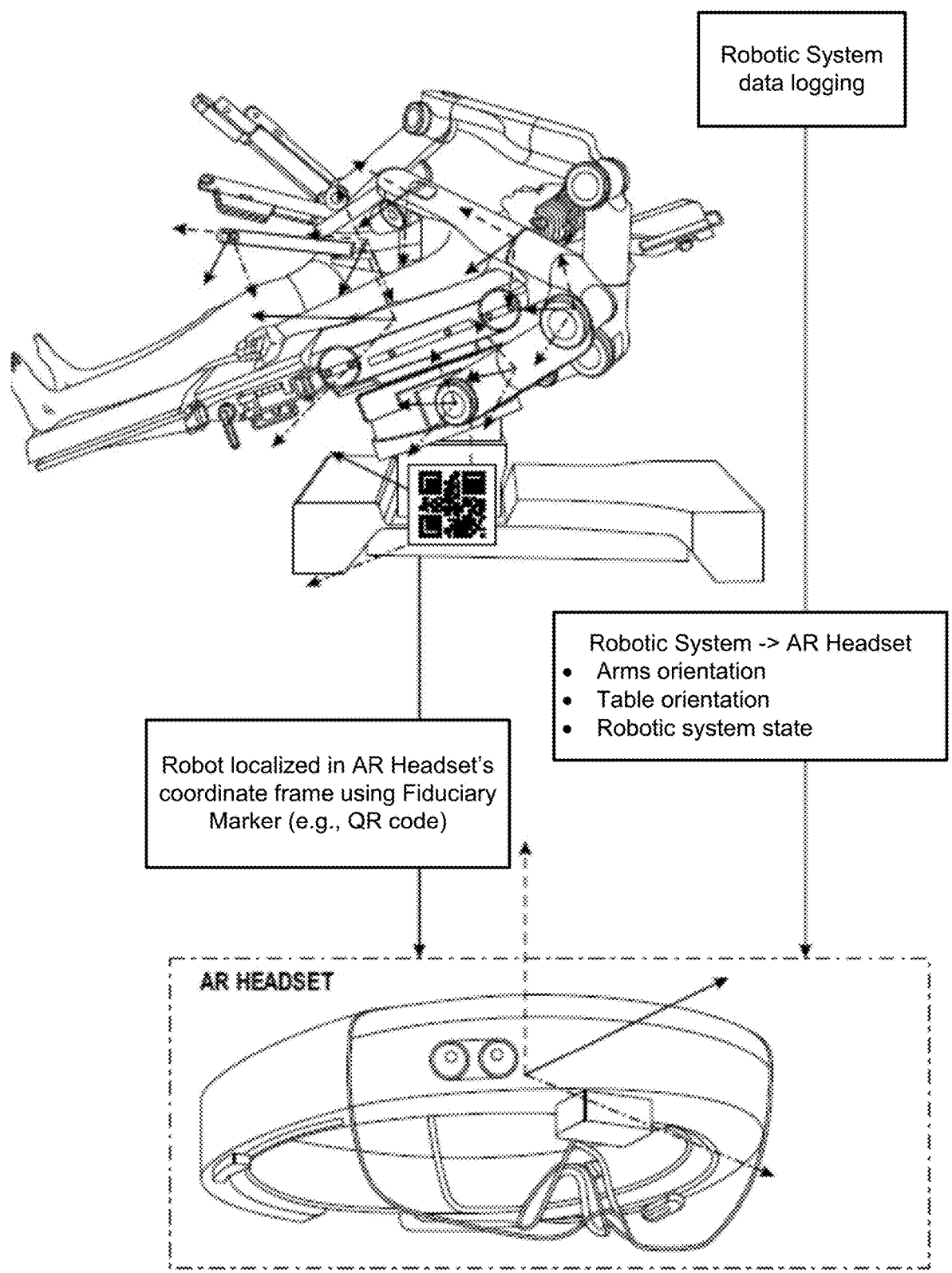
FIG. 6 shows the information exchange between an augmented reality headset and the surgical robotic system for the augmented reality headset to display spatial, system, and temporal information of the components of the surgical robotic system in the coordinate frame of the augmented reality headset based on establishing a common coordinate frame between the augmented reality headset and the surgical robotic system using fixed fiduciary markers, in accordance with aspects of the subject technology.

FIG. 6 shows the information exchange between an augmented reality headset and the surgical robotic system 1 for the augmented reality headset to display spatial, system, and temporal information of the components of the surgical robotic system 1 in the coordinate frame of the augmented reality headset based on establishing a common coordinate frame between the augmented reality headset and the surgical robotic system 1 using fixed fiduciary markers, in accordance with aspects of the subject technology. In contrast to the surgical robotic system 1 of FIG. 2, the surgical robotic system 1 of FIG. 6 lacks a suite of RGBD sensors to capture images of the surgical robotic system 1 that may be analyzed with the point cloud from the RGBD sensor of the headset to establish a common coordinate frame between the AR headset and the surgical robotic system 1.

Instead, to establish the position and orientation information of the arms 4 and table 5 in the AR headset's coordinate frame, the AR headset may capture one or more predetermined and fixed fiduciary markers on the bed 5. In one embodiment, the fiduciary markers may be QR codes. The locations of the fiduciary markers may be known based on the coordinate frame of the surgical robotic system 1. By analyzing the RGBD image of the fiduciary markers in the coordinate frame of the AR headset based on the knowledge of the fixed locations of the fiduciary markers in the coordinate frame of the surgical robotic system 1, the AR headset may establish the common coordinate frame between the AR headset and the surgical robotic system 1. In one embodiment, the AR headset may transmit the point cloud of the fiduciary markers to the surgical robotic system 1 for the surgical robotic system 1 to establish the common coordinate frame. In one embodiment, the AR headset may run an object recognition algorithm on the RGBD images of the surgical robotic system 1 to recognize the arms 4 and table 5. In one embodiment, the surgical robotic system 1 may have both the suite of RGBD sensors of FIG. 2 and the fixed fiduciary markers. The images of the fiduciary markers as well as the images of the arms 4 and table 5 captured by the RGBD sensor of the AR headset may be analyzed in tandem with the images captured by the RGBD sensors of the surgical robotic system 1 to establish the common coordinate frame between the AR headset and the surgical robotic system 1.

Once the common coordinate frame is established, the surgical robotic system 1 may transmit information to the AR headset for the AR headset to create 3D virtual models of the arms 4 and table 5 that match their actual positions and orientations, or to create 3D virtual models of the arms 4 and table 5 that may be fused with their real-time real-scene positions and orientations. In one embodiment, the surgical robotic system 1 may transmit to the AR headset real-time information of the positions and orientations of the arms 4 and the table 5, 3D mesh model of components of the surgical robotic system 1 or the operating room, real-time system state information of the surgical robotic system 1, etc.

The SLAM algorithm running on the AR headset may localize the virtual position and orientation of the arms 4, table 5, and other components of the surgical robotic system 1 as the coordinate frame of the AR headset changes relative to the surgical robotic system 1. The AR headset may render context-sensitive information of the arms 4 and the table 5 based on the real-time information received from the surgical robotic system 1. The context-sensitive information may be positioned relative to the arms 4 and table 5 to guide the wearer in configuring, operating, or troubleshooting the surgical robotic system 1 prior to, during, or after surgery.

The AR headset may provide other features such as a Web portal (e.g. browser), and may display information such as case setups, surgeon preference cards, instrument lives, documentation, snap shots from endoscope for documentation, photos of patients for documentation, patient data, etc. Other features may include teleconferencing using microphones, speakers, a back facing webcam; user authentication using a fingerprint reader and/or an NFC card reader; range detection of the AR headset to control tower 3 using Bluetooth and WiFi to monitor signal strengths of the connections and to trigger alerts when the interface device is too far away.

Figure 7:
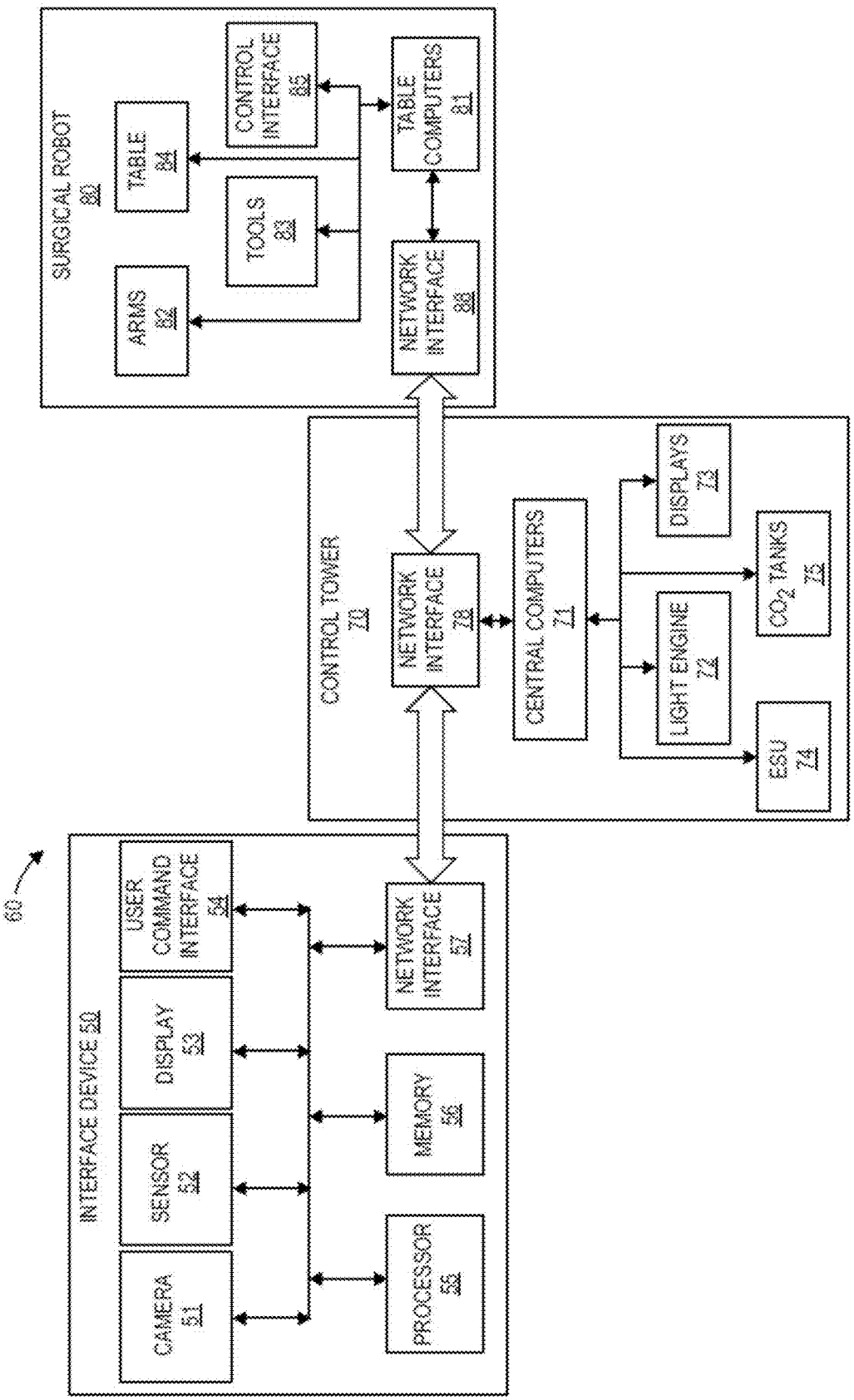
FIG. 7 is a block diagram illustrating exemplary hardware components of an augmented reality headset and a surgical robotic system, in accordance with aspects of the subject technology.

FIG. 7 is a block diagram illustrating exemplary hardware components of an AR headset 60 and a surgical robotic system, in accordance with aspects of the subject technology. The surgical robotic system may include a surgical robot 80, and a control tower 70. The surgical robotic system may include other or additional hardware components; thus, the diagram is provided by way of example and not a limitation to the system architecture.

The AR headset 60 includes a camera 51, sensor 52, display 53, user command interface 54, processor 55, memory 56, and network interface 57. The camera 51 and the sensor 52 may be configured as RGBD sensors to capture color images and depth-image information of the surgical robotic system. Images captured by the camera 51 and sensor 52 or virtual images rendered by the AR headset 60 may be projected on the display 53.

The processor 55 may be configured to run image processing algorithms to process the images captured by the camera 51 and the sensor 52 to automatically identify a component of the surgical robot 80 such as arms 4 or bed 5. In one embodiment, based on real-time system state information received from the surgical robotic system (e.g., control tower 70) and a common coordinate frame between the AR headset 60 and the surgical robot 80, the processor 55 may be configured to create 3D virtual models of components of surgical robot 80 that match their actual positions and orientations, or to create 3D virtual models of components of the surgical robot 80 that may be fused with their real-time real-scene positions and orientations. In one embodiment, the processor 55 may run the SLAM algorithm to localize the virtual position and orientation of the components of the surgical robot 80 as the coordinate frame of the AR headset 60 changes relative to the coordinate frame of the surgical robot 80. The processor 55 may be configured to run an operating system to control the operation of the interface device 50. The memory 56 may store the image processing algorithms, virtual image rendering algorithm, SLAM algorithm, operating system, program codes, and other data memories used by the processor 55.

The user command interface 54 may include the interface for other features such as the Web portal. The hardware components may communicate via a bus. The interface device may use the network interface 57 to communicate with the surgical robotic system through an external interface 58. The external interface 58 may be a wireless or a wired interface.

The control tower 70 may be a mobile point-of-care cart housing touchscreen displays, computers that control the surgeon's robotically-assisted manipulation of instruments, computers to establish a common coordinate frame between the surgical robot 80 and the AR headset 60, safety systems, graphical user interface (GUI), light source, and video and graphics computers. The control tower 70 may comprise central computers 71 that may include at least a visualization computer, a control computer, and an auxiliary computer, various displays 73 that may include a team display and a nurse display, and a network interface 78 coupling the control tower 70 to both the AR headset 60 and the surgical robot 80. The control tower 70 may also house third-party devices, such as an advanced light engine 72, an electrosurgical generator unit (ESU) 74, and insufflator and CO2 tanks 75. The control tower 70 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 80 comprises an articulated operating table 84 with a plurality of integrated arms 82 that may be positioned over the target patient anatomy. A suite of compatible tools 83 may be attached to or detached from the distal ends of the arms 82, enabling the surgeon to perform various surgical procedures. The surgical robot 80 may also comprise control interface 85 for manual control of the arms 82, operating table 84, and tools 83. The control interface 85 may include items such as, but not limited to, remote controls, buttons, panels, and touchscreens. Other accessories such as trocars (sleeves, seal cartridge, and obturators) and drapes may also be manipulated to perform procedures with the system. In one embodiment, the plurality of the arms 82 may include four arms mounted on both sides of the operating table 84, with two arms on each side. For certain surgical procedures, an arm mounted on one side of the operating table 84 may be positioned on the other side of the operating table 84 by stretching out and crossing over under the operating table 84 and arms mounted on the other side, resulting in a total of three arms positioned on the same side of the operating table 84. The surgical tool may also comprise table computers 81 and a network interface 88, which may place the surgical robot 80 in communication with the control tower 70.

Figure 8:
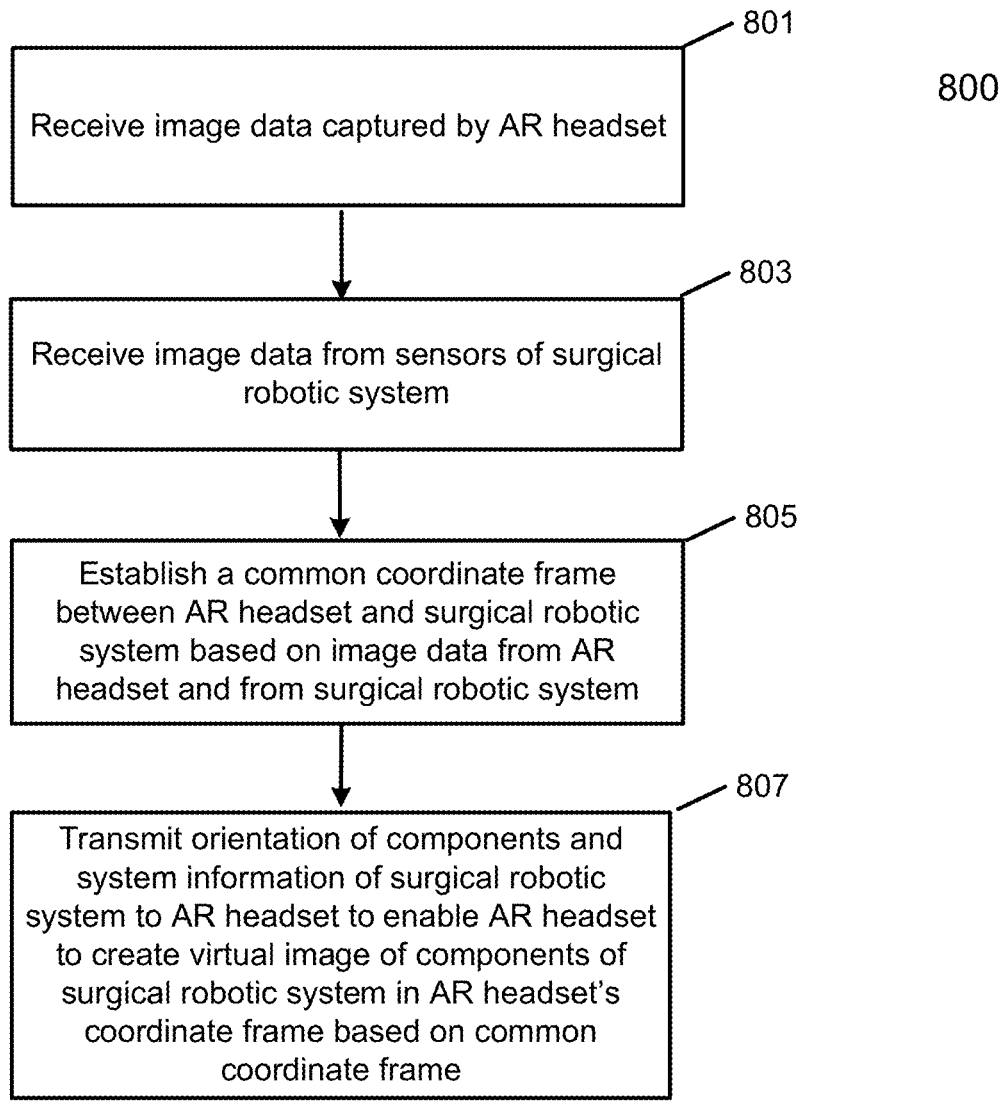
FIG. 8 is a flow chart illustrating a method of a surgical robotic system exchanging information with an augmented reality headset to establish a common coordinate frame between the augmented reality headset and the surgical robotic system and to transmit spatial, system, and temporal information of the components of the surgical robotic system to the augmented reality headset for rendering the components and system information as virtual images, in accordance with aspects of the subject technology.

FIG. 8 is a flow chart 800 illustrating a method of a surgical robotic system exchanging information with an AR headset to establish a common coordinate frame between the AR headset and the surgical robotic system and to transmit spatial, system, and temporal information of the components of the surgical robotic system to the AR headset for rendering the components and system information as virtual images, in accordance with aspects of the subject technology. The surgical robotic system may be the surgical robotic system of FIG. 2, 6 or 7.

In block 801, the surgical robotic system receives image data captured by the AR headset. In one embodiment, the image data may be RGBD image data of arms and table of the surgical robotic system captured by the RGBD sensors of the AR headset. The image data is based on the coordinate frame of the AR headset.

In block 803, the surgical robotic system receives image data captured by the surgical robotic system. In one embodiment, the image data may be RGBD image data of arms and table of the surgical robotic system captured by the RGBD sensors of the surgical robotic system. The image data is based on the coordinate frame of the surgical robotic system.

In block 805, the surgical robotic system establishes a common coordinate frame between the AR headset and the surgical robotic system based on the image data from the AR headset and the image data captured by the surgical robotic system. In one embodiment, the surgical robotic system may process the image data of the arms and table from the AR headset based on the coordinate frame of the AR headset, the image data of the arms and table captured by the surgical robotic system based on the coordinate frame of the surgical robotic system, and real-time data stream that describes the position and orientation information of the arms and table to recognize and virtually establish the 3D positions and orientations of the arms and table in the AR headset's coordinate frame.

In block 807, the surgical robotic system transmits to the AR headset real-time information of the surgical robotic system based on the common coordinate frame to enable the AR headset to create 3D virtual models of components of the surgical robotic system in the AR headset's coordinate frame. In one embodiment, the real-time information of the surgical robotic system may include real-time information of the positions and orientations of the arms and the table, analyzed results of the image data received from the AR headset, 3D mesh model of components of the surgical robotic system, real-time system state information of the surgical robotic system, etc. In one embodiment, the real-time system state information of the surgical robotic system may include joint angles and degrees of rotations of the arms, types of tools attached to the arms, tool grasp status, active tool energy, arm mode, troubleshooting error codes, etc. The AR headset may create 3D virtual models of the arms and table that match their actual positions and orientations, 3D virtual models of target positions and orientations of the arms and table that may be fused with their real-time real-scene positions and orientations, or other context-sensitive information about the arms and table.

The real-time information of the surgical robotic system based on the common coordinate frame transmitted by the surgical robotic system to the AR headset may be used by the AR headset to maintain positions and orientations of the components of the surgical robotic system such as the arms and table as the coordinate frame of the AR headset changes relative to the surgical robotic system. In one embodiment, a SLAM algorithm may run on the AR headset to localize the position and orientation of the AR headset so the virtual images of the components of the surgical robotic system are spatially-fixed to maintain their virtual positions and orientations as the wearer moves about in the operating room. For example, virtual recreation of the arms and table may match the real-time real-scene positions and orientations of the arms and table as the coordinate frame of the AR headset changes relative to the coordinate frame of the surgical robotic system.

Figure 9:
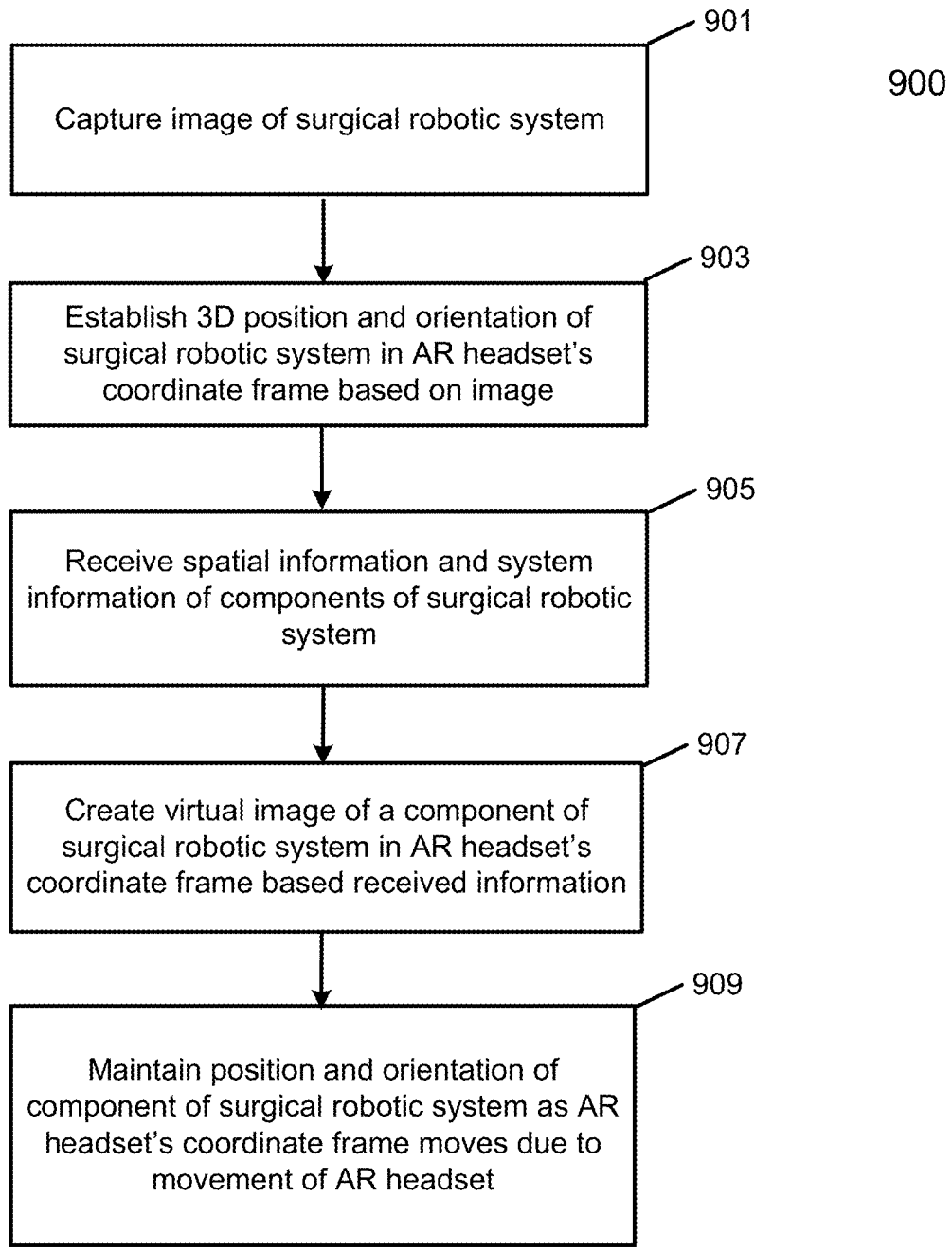
FIG. 9 is a flow chart illustrating a method of an augmented reality headset to establish a common coordinate frame between the augmented reality headset and the surgical robotic system using fixed fiduciary markers and to receive spatial, system, and temporal information of the components of the surgical robotic system for rendering an image, in accordance with aspects of the subject technology.

FIG. 9 is a flow chart illustrating a method 900 of an AR headset to establish a common coordinate frame between the AR headset and the surgical robotic system and to receive spatial, system, and temporal information of the components of the surgical robotic system for rendering the components and system information as virtual images, in accordance with aspects of the subject technology. The AR headset may be the AR headset of FIG. 2, 6 or 7.

In block 901, the AR headset captures image data of the surgical robotic system. In one embodiment, the image data may be RGBD image data of arms and table of the surgical robotic system captured by the RGBD sensors of the AR headset. In one embodiment, the image data may be RGBD image data of pre-determined and fixed fiduciary markers (e.g., QR codes) displayed on the surgical robotic system. The image data is based on the coordinate frame of the AR headset.

In block 903, the AR headset establishes the 3D position and orientation of the surgical robotic system in the AR headset's coordinate frame based on the captured image data. A global coordinate frame for the AR headset and the surgical robotic system may be established for virtual components of the surgical robotic system to be created or rendered in the AR headset's coordinate frame. In one embodiment, the AR headset may transmit the RGBD image data of arms and table of the surgical robotic system to the surgical robotic system. The surgical robotic system may establish a common coordinate frame between the AR headset and the surgical robotic system based on the image data of the arms and table from the AR headset based on the coordinate frame of the AR headset, image data of the arms and table captured by the surgical robotic system based on the coordinate frame of the surgical robotic system, and real-time data stream that describes the position and orientation information of the arms and table.

In one embodiment, the AR headset may analyze the RGBD image of the fiduciary markers in the coordinate frame of the AR headset based on the knowledge of the fixed locations of the fiduciary markers in the coordinate frame of the surgical robotic system to establish the common coordinate frame between the AR headset and the surgical robotic system.

In block 905, the AR headset receives from the surgical robotic system real-time information of the surgical robotic system. In one embodiment, real-time the information of the surgical robotic system may include real-time information of the positions and orientations of the arms and the table, analyzed results of the image data received from the AR headset, 3D mesh model of components of the surgical robotic system, real-time system state information of the surgical robotic system, etc. In one embodiment, the real-time system state information of the surgical robotic system may include joint angles and degrees of rotations of the arms, types of tools attached to the arms, tool grasp status, active tool energy, arm mode, troubleshooting error codes, etc. In one embodiment, if the surgical robotic system establishes the common coordinate frame between the AR headset and the surgical robotic system, the information received from the surgical robotic system may have been translated by the surgical robotic system to the AR headset's coordinate frame. In one embodiment, if the AR headset establishes the common coordinate frame between the AR headset and the surgical robotic system using the fiduciary markers, the information received from the surgical robotic system may be in the surgical robotic system's coordinate frame. The AR headset may translate the information from the surgical robotic system's coordinate frame to the AR headset's coordinate frame based on the common coordinate frame.

In block 907, the AR headset may create 3D virtual models of components of the surgical robotic system in the AR headset's coordinate frame based on the received information. In one embodiment, The AR headset may create 3D virtual models of the arms and table that match their actual positions and orientations, 3D virtual models of target positions and orientations of the arms and table that may be fused with their real-time real-scene positions and orientations, or other context-sensitive information about the arms and table. In one embodiment, the context-sensitive information may be positioned relative to the arms and table 5 guide the wearer in configuring, operating, or troubleshooting the surgical robotic system prior to, during, or after surgery.

In block 909, the AR headset maintains positions and orientations of the components of the surgical robotic system such as the arms and table as the coordinate frame of the AR headset changes relative to the surgical robotic system. In one embodiment, a SLAM algorithm may run on the AR headset to localize the position and orientation of the AR headset so the virtual images of the components of the surgical robotic system are spatially-fixed to maintain their virtual positions and orientations as the wearer moves about in the operating room. For example, virtual recreation of the arms and table may match the real-time real-scene positions and orientations of the arms and table as the coordinate frame of the AR headset changes relative to the coordinate frame of the surgical robotic system.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

The invention claimed is:

1. An augmented reality (AR) device for a surgical robotic system, comprising:
    a sensor configured to capture image data of a first component of the surgical robotic system;
    a processor configured to:
        establish a global coordinate frame for the AR device and the surgical robotic system based on the image data for virtual components of the surgical robotic system to be created in the coordinate frame of the AR device;
        receive spatial information and real-time system state information of the surgical robotic system; and
        create a three-dimensional (3D) virtual model of a second component of the surgical robotic system in the coordinate frame of the AR device based on the spatial information and the real-time system state information of the surgical robotic system and based on the global coordinate frame; and
    a display configured to present the 3D virtual model of the second component of the surgical robotic system.

2. The AR device of claim 1, wherein the processor configured to establish the global coordinate frame for the AR device and the surgical robotic system comprises:
    transmit, by the AR device, the image data of the first component to the surgical robotic system for the surgical robotic system to establish the global coordinate frame for the coordinate frame of the AR device and a coordinate frame of the surgical robotic system.

3. The AR device of claim 2, wherein the spatial information of the surgical robotic system is received in the coordinate frame of the AR device.

4. The AR device of claim 1, wherein the first component of the surgical robotic system is a fiduciary marker of the surgical robotic system, and wherein the processor configured to establish the global coordinate frame for the AR device and the surgical robotic system comprises:
    analyze the image data of the fiduciary marker based on a fixed location of the fiduciary marker in a coordinate frame of the surgical robotic system to establish the global coordinate frame for the coordinate frame of the AR device for the coordinate frame of the surgical robotic system.

5. The AR device of claim 4, wherein the spatial information of the surgical robotic system comprises spatial information of the second component in the coordinate frame of the surgical robotic system, and wherein the processor configured to create the 3D virtual model of the second component of the surgical robotic system in the coordinate frame of the AR device comprises:
    translate the spatial information of the second component in the coordinate frame of the surgical robotic system to the coordinate frame of the AR device based on the global coordinate frame.

6. The AR device of claim 1, further comprising the processor configured to maintain a position and orientation of the 3D virtual model of the second component of the surgical robotic system as the coordinate frame of the AR device changes relative to a coordinate frame of the surgical robotic system.

7. The AR device of claim 1, wherein the spatial information of the surgical robotic system comprises spatial information of the second component, and wherein the processor configured to create the 3D virtual model of the second component comprises:
    create a position and orientation of the second component of the surgical robotic system in the coordinate frame of the AR device based on the spatial information of the second component, wherein the position and orientation of the second component in the coordinate frame of the AR device matches an actual position and orientation of the second component or a target position and orientation of the second component.

8. The AR device of claim 7, wherein the real-time system state information of the surgical robotic system comprises real-time system state information of the second component, and wherein the processor configured to create the 3D virtual model of the second component further comprises:
create context-sensitive information of the second component of the surgical robotic system based on the real-time system state information of the second component.

9. The AR device of claim 1, wherein the second component of the surgical robotic system comprises a robotic arm or an operating table of the surgical robotic system.

10. The AR device of claim 9, wherein the 3D virtual model of the second component comprises:
a 3D virtual rendering of a position and orientation of the robotic arm or the operating table; and
visual or audible communication of the real-time system state information of the robotic arm or the operating table.

11. A method comprising:
capturing, using a sensor of an augmented reality (AR) device, image data of a first component of a surgical robotic system;
establishing a global coordinate frame for the AR device and the surgical robotic system based on the image data for virtual components of the surgical robotic system to be created in the coordinate frame of the AR device;
receiving spatial information and real-time system state information of the surgical robotic system;
creating a three-dimensional (3D) virtual model of a second component of the surgical robotic system in the coordinate frame of the AR device based on the spatial information and the real-time system state information of the surgical robotic system and based on the global coordinate frame; and
presenting, on a display of the AR device, the 3D virtual model of the second component of the surgical robotic system.

12. The method of claim 11, wherein establishing the global coordinate frame for the AR device and the surgical robotic system comprises transmitting, by the AR device, the image data of the first component to the surgical robotic system for the surgical robotic system to establish the global coordinate frame for the coordinate frame of the AR device and a coordinate frame of the surgical robotic system.

13. The method of claim 12, wherein the spatial information of the surgical robotic system is received in the coordinate frame of the AR device.

14. The method of claim 11,
wherein the first component of the surgical robotic system is a fiduciary marker of the surgical robotic system, and
wherein establishing the global coordinate frame for the AR device and the surgical robotic system comprises analyzing the image data of the fiduciary marker based on a fixed location of the fiduciary marker in a coordinate frame of the surgical robotic system to establish the global coordinate frame for the coordinate frame of the AR device for the coordinate frame of the surgical robotic system.

15. The method of claim 14,
wherein the spatial information of the surgical robotic system comprises spatial information of the second component in the coordinate frame of the surgical robotic system, and
wherein creating the 3D virtual model of the second component of the surgical robotic system in the coordinate frame of the AR device comprises translating the spatial information of the second component in the coordinate frame of the surgical robotic system to the coordinate frame of the AR device based on the global coordinate frame.

16. The method of claim 11 further comprising maintaining a position and orientation of the 3D virtual model of the second component of the surgical robotic system as the coordinate frame of the AR device changes relative to a coordinate frame of the surgical robotic system.

17. The method of claim 11, wherein the second component of the surgical robotic system comprises a robotic arm or an operating table of the surgical robotic system.

18. The method of claim 17, wherein the 3D virtual model of the second component comprises:
a 3D virtual rendering of a position and orientation of the robotic arm or the operating table; and
visual or audible communication of the real-time system state information of the robotic arm or the operating table.

19. A surgical robotic system comprising:
a first component and a second component;
an augmented reality (AR) device that comprises a sensor configured to capture image data of the first component, and a display;
one or more processors; and
memory having instructions stored therein which when executed by the one or more processors causes the surgical robotic system to:
establish a global coordinate frame for the AR device and the surgical robotic system based on the image data for virtual components of the surgical robotic system to be created in the coordinate frame of the AR device;
receive spatial information and real-time system state information of the surgical robotic system; and
create a three-dimensional (3D) virtual model of the second component in the coordinate frame of the AR device based on the spatial information and the real-time system state information of the surgical robotic system and based on the global coordinate frame,
wherein the display is configured to present the 3D virtual model of the second component.

20. The surgical robotic system of claim 19, wherein the first component comprises a fiduciary marker, and the second component comprises a robotic arm or an operating table of the surgical robotic system.

* * * * *